(12) United States Patent
Matzger et al.

(10) Patent No.: US 10,590,137 B2
(45) Date of Patent: Mar. 17, 2020

(54) MERCAPTOPURINE HEMIHYDRATE

(71) Applicant: THE REGENTS OF THE UNIVERSITY OF MICHIGAN, Ann Arbor, MI (US)

(72) Inventors: Adam J. Matzger, Ann Arbor, MI (US); Kortney Kersten, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/074,438

(22) PCT Filed: Feb. 2, 2017

(86) PCT No.: PCT/US2017/016109
§ 371 (c)(1),
(2) Date: Aug. 1, 2018

(87) PCT Pub. No.: WO2017/136488
PCT Pub. Date: Aug. 10, 2017

(65) Prior Publication Data
US 2019/0048010 A1 Feb. 14, 2019

Related U.S. Application Data

(60) Provisional application No. 62/290,093, filed on Feb. 2, 2016.

(51) Int. Cl.
*C07D 473/38* (2006.01)
*A61P 37/00* (2006.01)
*A61P 35/02* (2006.01)

(52) U.S. Cl.
CPC ............ *C07D 473/38* (2013.01); *A61P 35/02* (2018.01); *A61P 37/00* (2018.01); *C07B 2200/13* (2013.01)

(58) Field of Classification Search
CPC .................................................... C07D 473/38
USPC ....................................................... 514/263.3
See application file for complete search history.

(56) References Cited

U.S. PATENT DOCUMENTS

| 5,252,569 A | 10/1993 | Hajos et al. |
| 5,563,014 A | 10/1996 | Malhotra et al. |
| 2007/0073385 A1 | 3/2007 | Schaeffer et al. |
| 2010/0124544 A1 | 5/2010 | Kawasaki et al. |

OTHER PUBLICATIONS

Wikipedia, https://en.wikipedia.org/wiki/Mercaptopurine, visited Mar. 14, 2019.*
International Application No. PCT/US17/16109, International Search Report and Written Opinion, dated Apr. 14, 2017.
International Application No. PCT/US17/16109, International Preliminary Report on Patentability, dated Aug. 7, 2018.
Kersten et al., Improved pharmacokinetics of mercaptopurine afforded by a thermally robust hemihydrate, Chem. Commun. (Camb)., 52(30):5281-4 (Apr. 2016).
European Patent Application No. 17748107.4, Extended European Search Report, dated Jun. 12, 2019.
Huang et al., Polymorphic and dissolution properties of mercaptopurine, J. Pharm. Sci., 66(4):608-9 (Apr. 1977).
Kuroda et al., [Studies on drug nonequivalence. VIII. Solubilities of polymorphs and hydrate of mercaptopurine], Yakugaku Zasshi, 99(7):745-51 (Jul. 1979).
Wang et al., Polymorphic and dissolution properties of mercaptopurine, Bioorg. Med. Chem. Lett., 25(5):1042-5 (Jan. 2015).
Xu et al., Improving the solubility of 6-mercaptopurine via cocrystals and salts, Crystal Growth & Design, 12(12):6004-11 (Dec. 2012).

* cited by examiner

*Primary Examiner* — Taofiq A Solola
(74) *Attorney, Agent, or Firm* — Marshall, Gerstein & Borun LLP

(57) ABSTRACT

Provided herein is a new mercaptopurine form, as a hemihydrate, and methods of making and using the same.

10 Claims, 6 Drawing Sheets

MERCAPTOPURINE HEMIHYDRATE

STATEMENT OF US GOVERNMENT INTEREST

The invention was made with support from grant no. GM106180, awarded by the National Institutes of Health. The government has certain rights in this invention.

BACKGROUND

Mercaptopurine, which has a structure

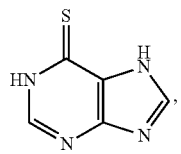

was developed in the 1950s, and was one of the first antileukemia drugs. Though the anhydrate structure is also known, mercaptopurine is sold as the monohydrate form under the commercial name of Purinethol. Mercaptopurine acts as a purine inhibitor in the body, and has shown high activity ($IC_{50}$=0.5 μM) in some cancer lines. However, the commercial form is plagued by low water solubility (0.249 mg/mL at 37° C.) which may affect its bioavailability. The anhydrous form is more soluble, but suffers from poor stability. Thus, a need exists for a mercaptopurine form that is both soluble and stable.

SUMMARY

Provided herein is mercaptopurine hemihydrate. The mercaptopurine hemihydrate can have a DSC thermogram as shown in FIG. 8. The mercaptopurine hemihydrate can have a dehydration temperature of greater than 200° C., or 240° C. The mercaptopurine hemihydrate can be crystalline and have at least 7 2Θ values selected from the group consisting of 10.59±0.1, 14.14±0.1, 15.86±0.1, 16.25±0.1, 18.83±0.1, 20.80±0.1, 20.42±0.1, 21.35±0.1, 24.93±0.1, 25.75±0.1, 26.02±0.1, 27.97±0.1, and 28.54±0.1°, as measured using $CuK_\alpha$ radiation. In some cases, the mercaptopurine hemihydrate has 2Θ values of 10.59±0.1, 14.14±0.1, 15.86±0.1, 16.25±0.1, 18.83±0.1, 20.80±0.1, 20.42±0.1, 21.35±0.1, 24.93±0.1, 25.75±0.1, 26.02±0.1, 27.97±0.1, and 28.54±0.1°, as measured using $CuK_\alpha$ radiation. In some cases, the mercaptopurine hemihydrate has a powder x-ray diffraction pattern as shown in FIG. 7. In some cases, the mercaptopurine hemihydrate has a crystal structure as represented by the following parameters as measured at 85K: a (Å) 9.361, b (Å) 11.069, c (Å) 13.091, α)(°) 90, β(°) 110.3, and γ)(°) 90. In some cases, the mercaptopurine hemihydrate has a Raman spectrum with wavenumber shifts of 444±2, 577±2, and 674±2 $cm^{-1}$, as measured using a 633 nm laser. In some cases, the mercaptopurine hemihydrate has a Raman spectrum as shown in FIG. 4.

Also provided is a pharmaceutical composition comprising mercaptopurine hemihydrate as disclosed herein. The composition comprises mercaptopurine as active pharmaceutical ingredient (API) and a pharmaceutically acceptable excipient, wherein the API is at least 95% mercaptopurine hemihydrate. In some cases, the API is at least 99% mercaptopurine hemihydrate. The composition can be an oral composition.

Further provided herein are methods of treating cancer or an autoimmune disorder comprising administering mercaptopurine hemihydrate or a composition as disclosed herein to a subject in need thereof. In some cases, the subject suffers from cancer. In some embodiments, the cancer is acute lymphocytic leukemia (ALL) or chronic myeloid leukemia (CML). The method can further comprise administering an anticancer agent. In some cases, the anticancer agent comprises methotrexate. In some cases, the method is to treat an autoimmune disorder and the subject suffers from an autoimmune disorder. The autoimmune disorder can be Crohn's disease or ulcerative colitis.

Also provided herein are methods of making mercaptopurine hemihydrate comprising dissolving mercaptopurine monohydrate in methanol to form a methanol solution, contacting the methanol solution with water to form a solution, and crystallizing the mercaptopurine hemihydrate from the solution. In some cases, the mercaptopurine hemihydrate is crystallized as yellow needles. In various cases, the ratio (parts per volume) of methanol to water in the solution is 100:1 to less than 2:1. In some cases, the ratio is 50:1 to 5:1.

DETAILED DESCRIPTION

Figure 1:
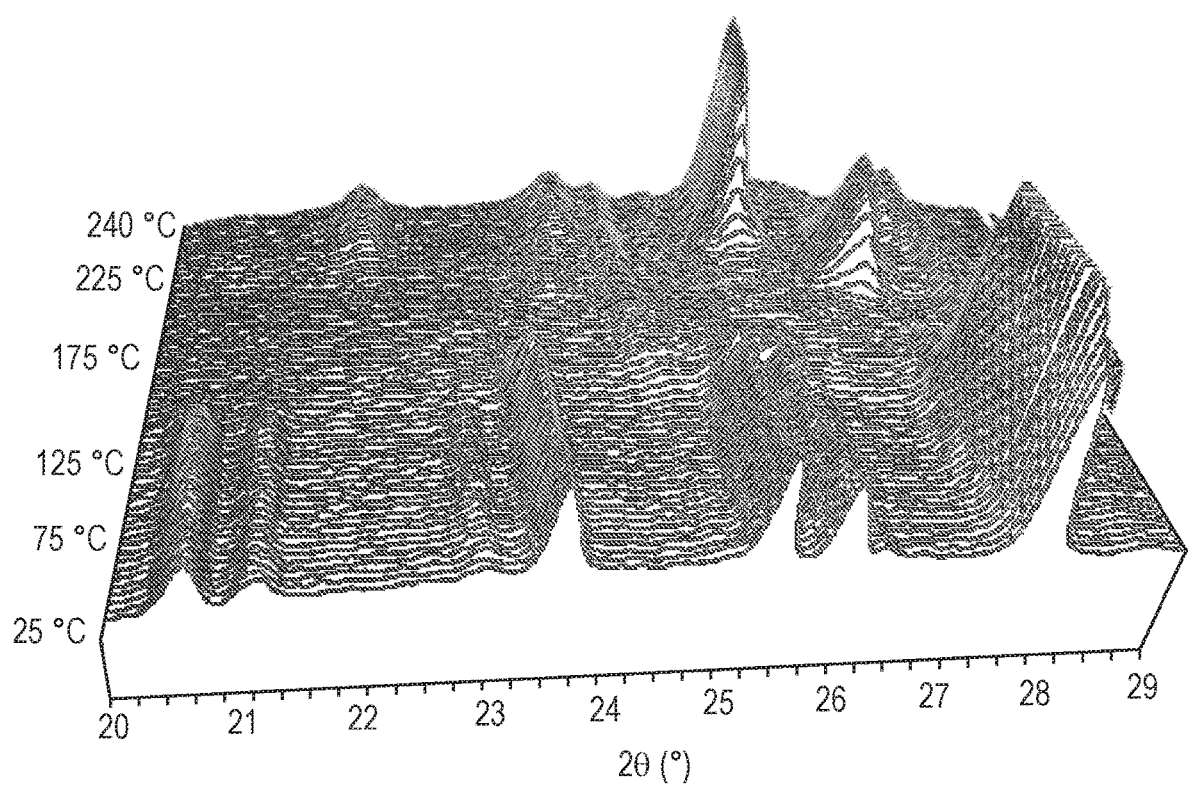
FIG. 1 shows variable temperature powder x-ray diffraction (PXRD) patterns for mercaptopurine monohydrate.

Solvated forms of drugs are commonly encountered during solid form discovery efforts. Hydrates, in particular, are of significance due to their impact on the properties of active pharmaceutical ingredients (APIs) and the potential for them to form in vivo. Water can fill gaps in the crystal structure of a compound, as well as stabilize a solid state arrangement through hydrogen bonding with API molecules. The presence of water in a crystal structure can also have an effect on the physical properties such as the solubility and thermal stability of the compound. While not always the case, the more water that is incorporated into the solid state structure of a compound, the lower its water solubility typically is. Therefore, it would seem that the anhydrous form of a compound would most often be the obvious choice for commercialization. However, almost half of pharmaceuticals with a known hydrate form are used commercially as the hydrate.

When selecting the solid form of a pharmaceutical to develop into a dosage both stability and solubility are considered. Although solubility considerations tend to favor using anhydrous forms, the desire for stability during processing and storage may favor the development of solvates. During processing into tablets or capsules, APIs are subjected to different humidities, pressures, and temperatures that may alter their solid form. Choosing the most soluble form of a drug may allow it to change forms once processed and could lead to non-uniformity of dosage. For example, use of moxifloxacin hydrochloride led to inconsistent active content during administration, a problem that was overcome with use of a novel hydrate. For these reasons, determining the resistance of a compound to changes in hydration state under different temperature and water activities is just as important as solubility when considering the ideal form of a pharmaceutical.

Provided herein is a crystal structure and properties of a novel hemihydrate form of mercaptopurine. This hemihydrate form shows higher water solubility and bioavailability than the commercial monohydrate form. Moreover, this new form has a dehydration temperature of 240° C., which is the highest seen of any single component hydrate reported to date. This combination of solubility and stability may be useful from a pharmaceutical standpoint to increase the bioavailability of mercaptopurine.

Preparation of Mercaptopurine Hemihydrate

In order to access the hemihydrate form, careful consideration must be given to the solvent used and the amount of water introduced into the system. The hemihydrate crystal form was obtained by heating the hydrate form in methanol (4 mg/mL) at 80° C. for 30 minutes. This solution (4.5 mL) is filtered into a vial containing 0.5 mL water and allowed to sit in a capped vial at room temperature for two days. The hemihydrate can form as yellow clusters of needles. The ratio of methanol to water can be 100:1 to less than 2:1 (e.g., 3:1). In some cases, the ratio is 100:1 to 3:1, 100:1 to 4:1, or 50:1 to 5:1.

Crystal Form Analysis of Mercaptopurine Hemihydrate

Figure 10:
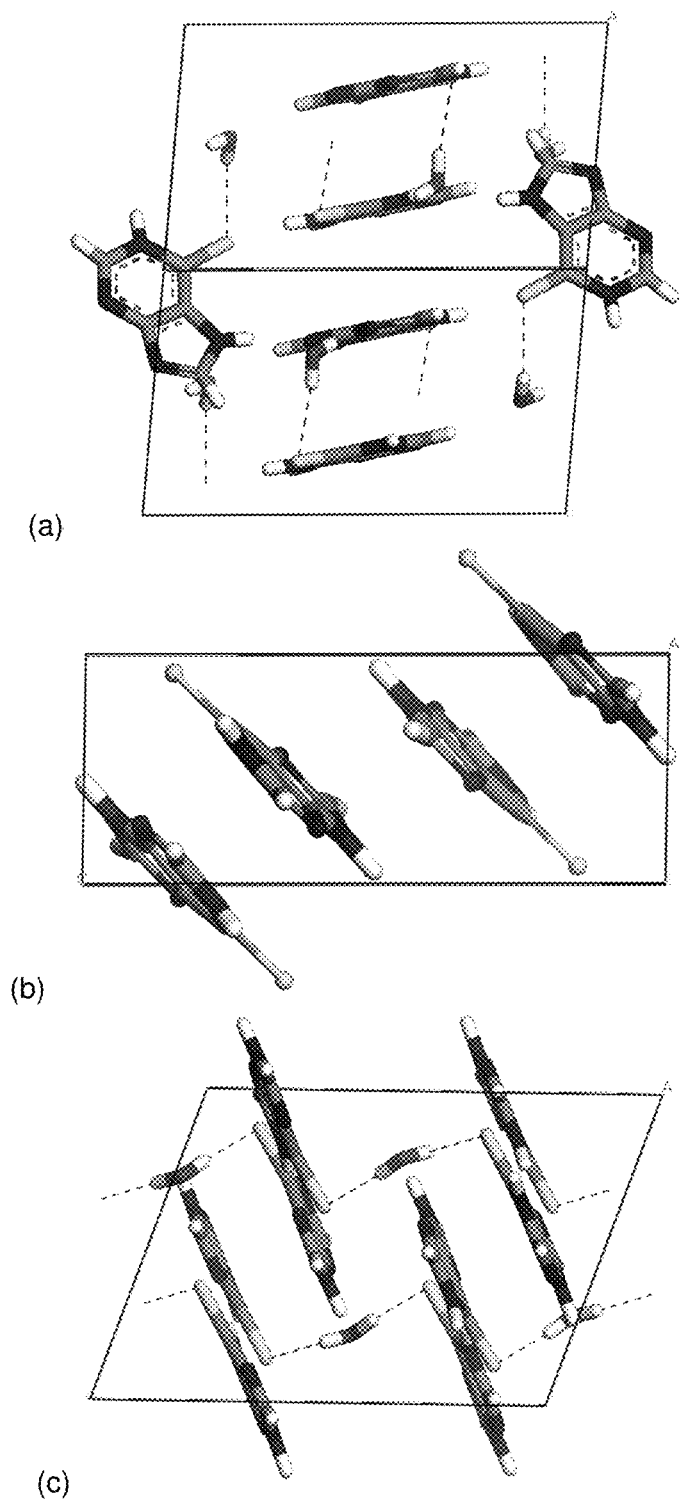
FIG. 10 shows a mercaptopurine hemihydrate crystal structure (a) in comparison to the known forms of (b) the anhydrate and (c) the hemihydrate.

Initial characterization of the novel form was performed by Raman spectroscopy as well as Powder X-ray Diffraction (PXRD). Characteristic differences are apparent between all three forms by Raman spectroscopy in the region of 350 to 750 cm$^{-1}$. Computation of the vibrational modes of the isolated molecule assigns the observed peaks in this region to different modes of ring deformation and hydrogen wagging, expected for molecules containing purine rings. These differences suggest alterations in packing between the three forms that restrict the ring breathing in various ways. The PXRD patterns of the hemihydrate and anhydrate, though similar, are easily distinguishable from the monohydrate. Similarities in the powder patterns between the hemihydrate and anhydrate structures suggest an isostructural relationship. However, minor differences can be seen in the 20 to 30° 2θ range. A single crystal of sufficient quality was isolated for structural determination and the hemihydrate structure is shown in FIG. 10 in comparison to the known forms the anhydrate, and the hemihydrate.

Investigation of the structures (hydrogen atom positions normalized in Mercury) indicates that the water molecules are incorporated into the structure differently in the monohydrate and hemihydrate forms. In the monohydrate, one water molecule hydrogen bonds to the sulfur of one mercaptopurine molecule (2.40 Å) and an imidazole nitrogen in another (1.82 Å). Two mercaptopurine molecules and two water molecules make a rhombus-shaped complex. These units are connected together into chains by hydrogen bonding between the oxygen of the water molecules and the pyrimidine N—H (1.75 Å). These two dimensional chains are linked through the imidazole N—H hydrogen bonds to a pyrimidine nitrogen in a mercaptopurine molecule of another chain at an N—H . . . N angle of 109° (1.90 Å). In the hemihydrate structure, however, one water molecule asymmetrically hydrogen bonds in between the sulfur atoms of two mercaptopurine molecules (2.37 and 2.45 Å) in a zigzag manner Two mercaptopurine molecules are then linked between both N—H(imidazole) . . . N(pyrimidine) sites with hydrogen bonds (1.87 and 1.88 Å). The zigzag chains are linked between N—H(pyrimidine) . . . N(imidazole) sites by hydrogen bonding (1.81 Å). The oxygen of the water molecule does not participate in hydrogen bonding in this structure. The sulfur centered hydrogen bonds (SCHBs) to water in each structure are very similar with distances consistent with moderate strength, and the monohydrate structure overall contains more hydrogen bonding; however, the hemihydrate form shows substantially increased thermal stability that is not explained by the aforementioned crystal packing.

Figure 2:
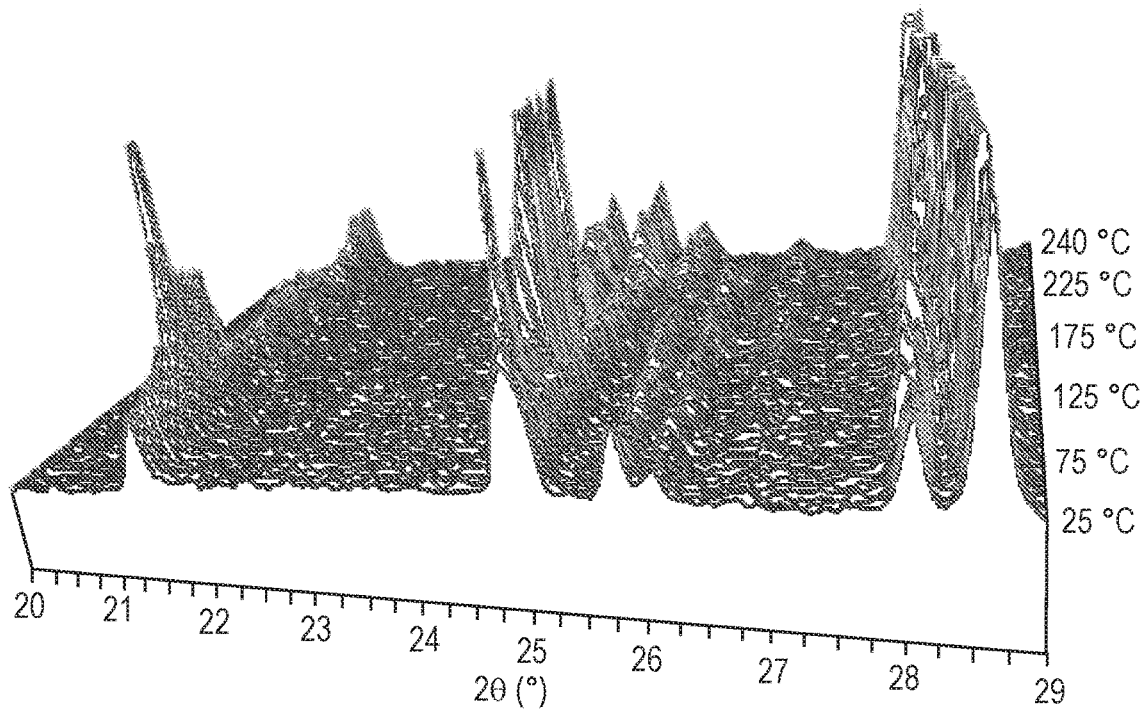
FIG. 2 shows variable temperature PXRD-patterns for the hemihydrate.

DSC analysis and variable temperature PXRD were used to analyse the thermally-induced phase transitions of the compounds. FIG. 1 shows variable temperature PXRD-patterns for the monohydrate, and FIG. 2 shows variable temperature PXRD-patterns for the hemihydrate. The monohydrate form shows a loss of crystallinity at ~160° C., corresponding with a loss of water, followed by a recrystallization into the anhydrate structure. In a sealed DSC pan, these events (water loss and loss of crystallinity) can be observed separately at ~140° C. and ~190° C., whereas in an open pan, they merge into one endothermic event with a $T_{max}$ of 177° C. The hemihydrate, however, does not show any loss of crystallinity during conversion to the anhydrate structure with water loss occurring in a sharp endothermic event at ~240° C. Additional energy is needed to remove water from the hemihydrate form, suggesting a greater stability to environmental conditions.

Figure 5:
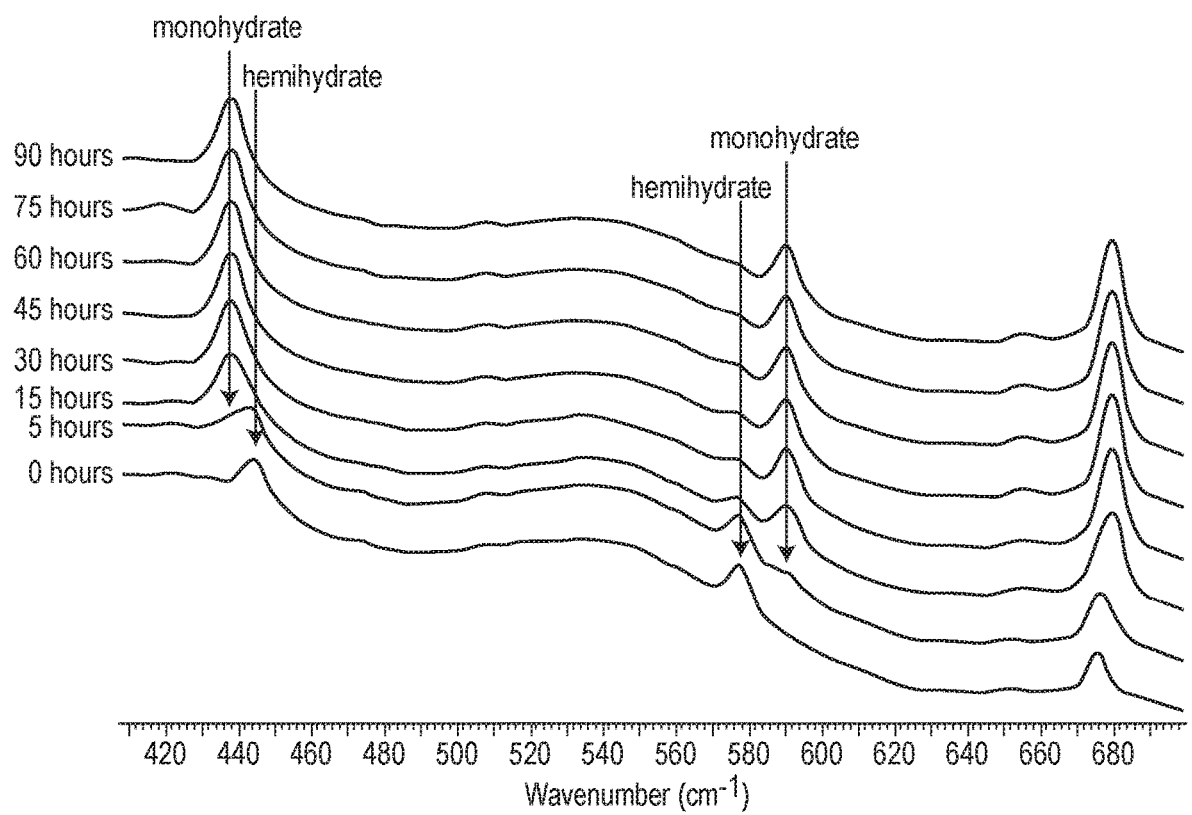
FIG. 5 shows Raman spectroscopy analysis of conversion of mercaptopurine hemihydrate over time (0 to 90 hours) to the monohydrate form.
Figure 6:
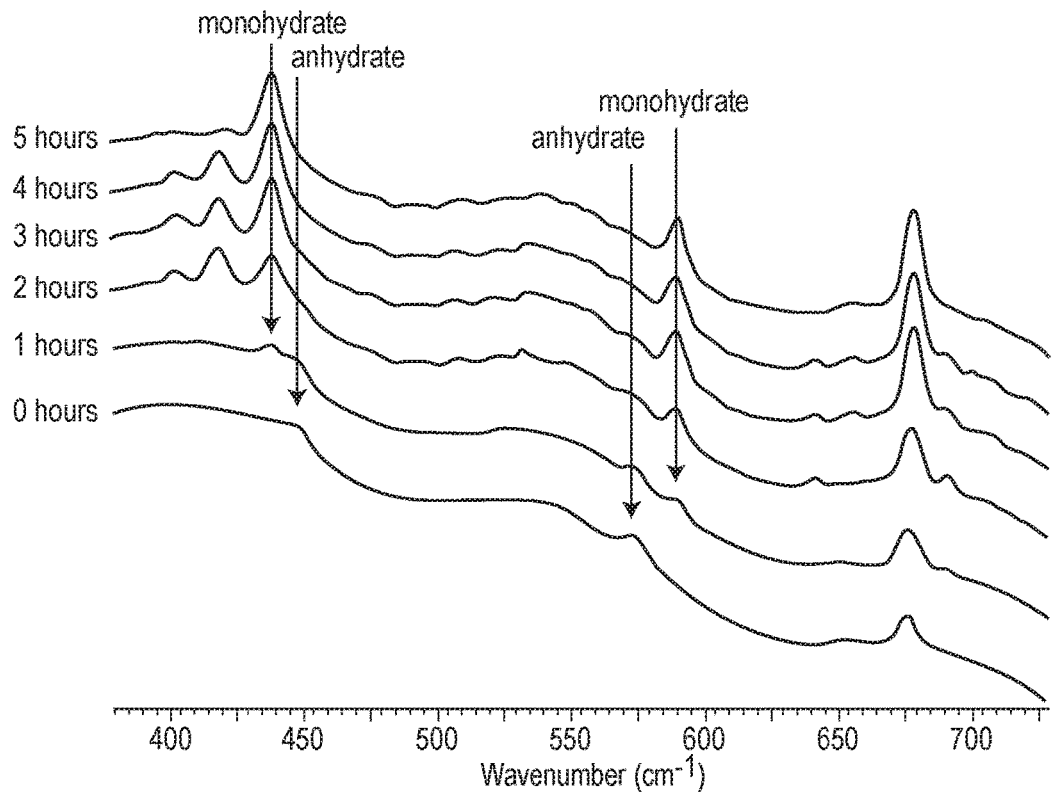
FIG. 6 shows Raman spectroscopy analysis of conversion of mercaptopurine anhydrate over time (0 to 5 hours) to the monohydrate form.
Figure 7:
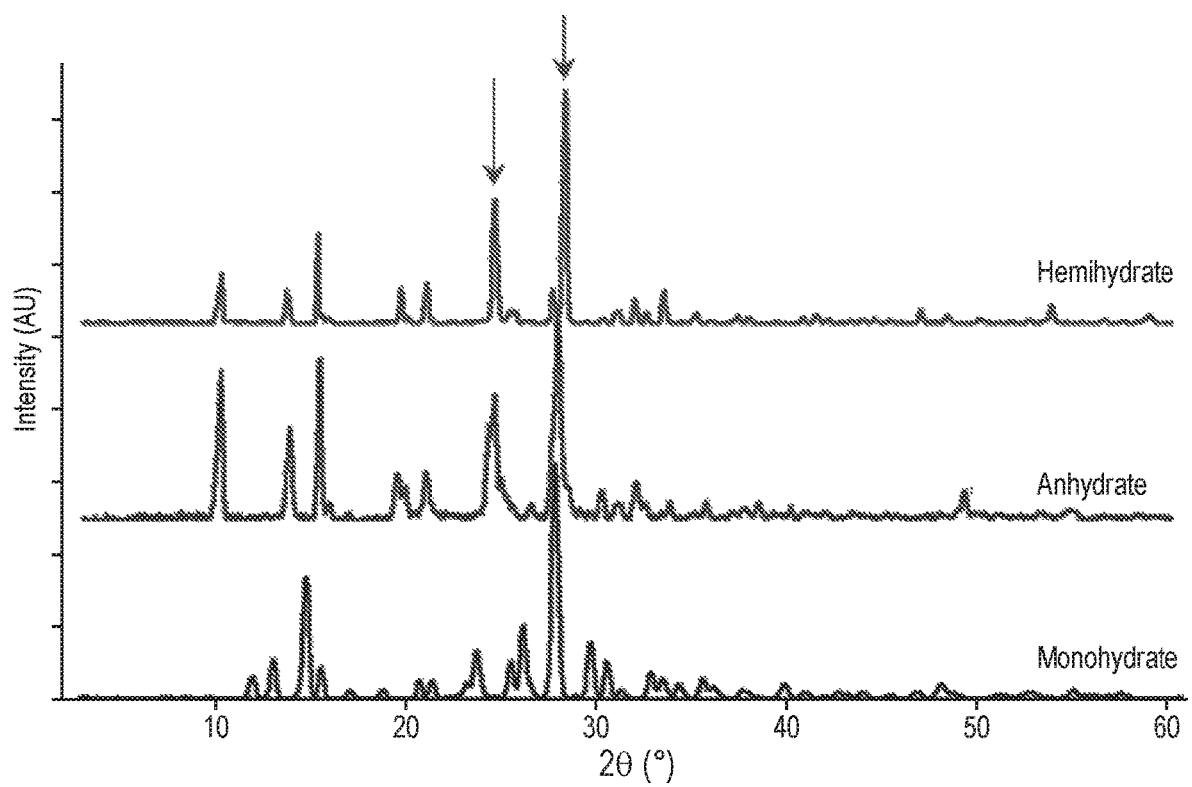
FIG. 7 shows room temperature PXRD patterns for each of mercaptopurine monohydrate, anhydrate, and hemihydrate.
Figure 8:
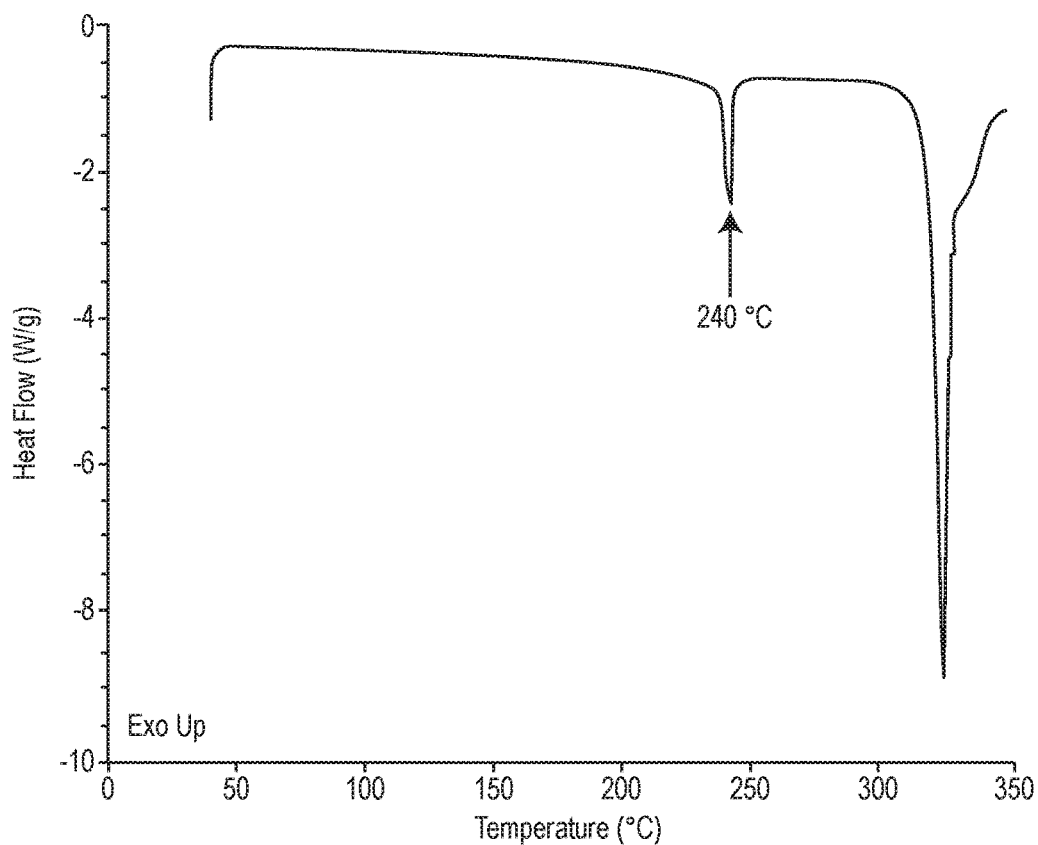
FIG. 8 shows differential scanning calorimetry (DSC) for mercaptopurine hemihydrate.
Figure 9:
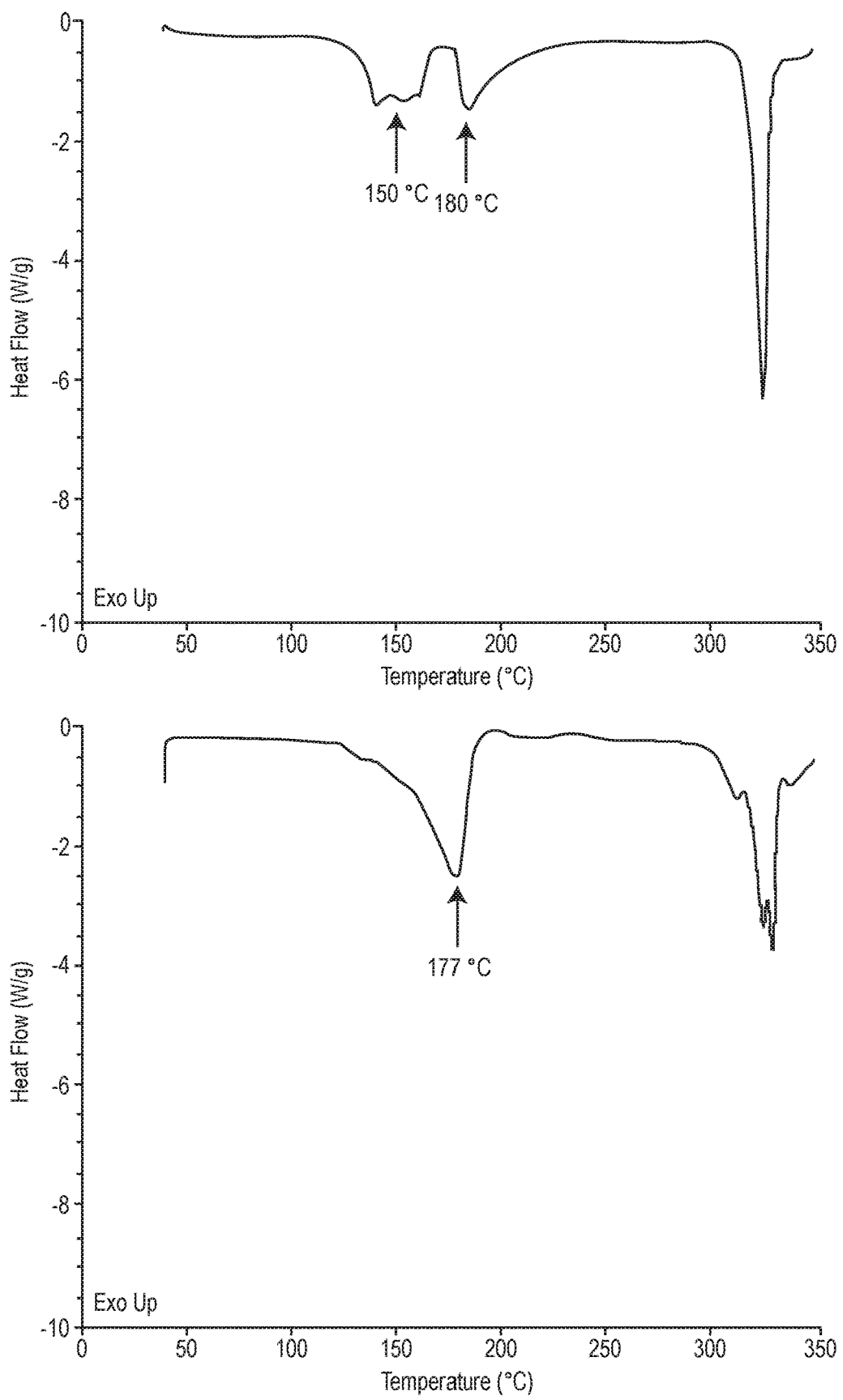
FIG. 9 shows DSC for mercaptopurine monohydrate with closed pan (top) and open pan (bottom).

In order to determine the stability to hydration, slurries of the anhydrate and hemihydrate forms were monitored using a non-contact Raman probe. While the anhydrate form converts to the monohydrate form in approximately 2-5 hours (see FIG. 6), the hemihydrate form is much more stable. It begins converting after approximately 5 hours, but does not fully convert to the monohydrate until approximately 70 hours (see FIG. 5). Overall, this shows that the hemihydrate form is significantly more stable in aqueous solutions than the anhydrate form, and while they will both transform to the monohydrate form eventually, the hemihydrate form takes much longer to do so. This suggest a potential advantage in making a more bioavailable formulation with the hemihydrate.

To determine the maximum solubility in water of all three forms of mercaptopurine, turbidity measurements were used to monitor particles in solution and determine the solubility at different temperatures. The monohydrate showed an average solubility of 0.249 mg/mL at 37° C., which is consistent with literature. The anhydrate showed an average solubility of 0.400 mg/mL at 37° C., approximately double that of the monohydrate, which is also consistent with previous reports. The hemihydrate form might be expected to have a solubility in between these two, but in fact shows a solubility very similar to the anhydrate, at 0.390 mg/mL at 37° C.

Figure 3:
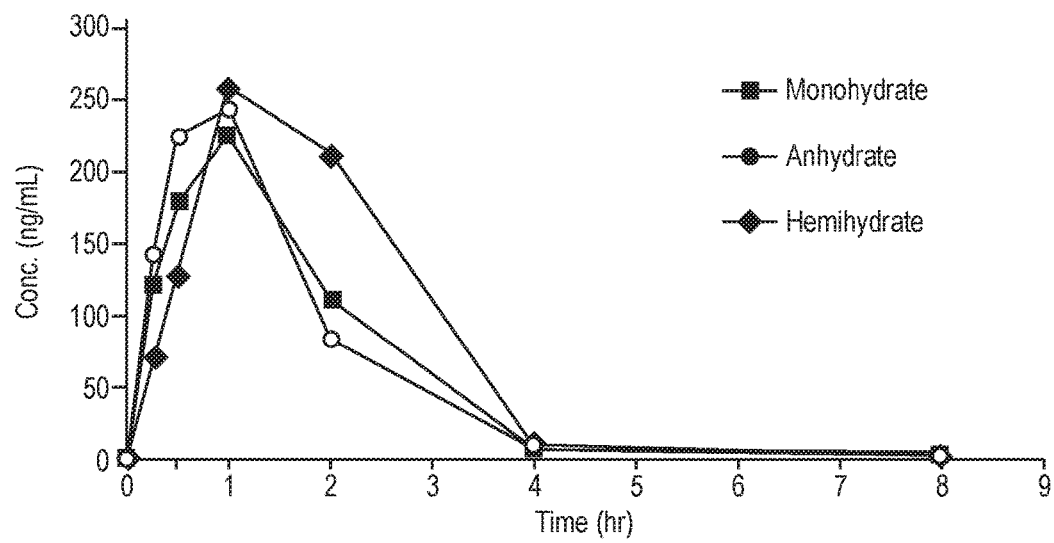
FIG. 3 shows pharmacokinetics of mercaptopurine monohydrate, anhydrate, and hemihydrate.
Figure 4:
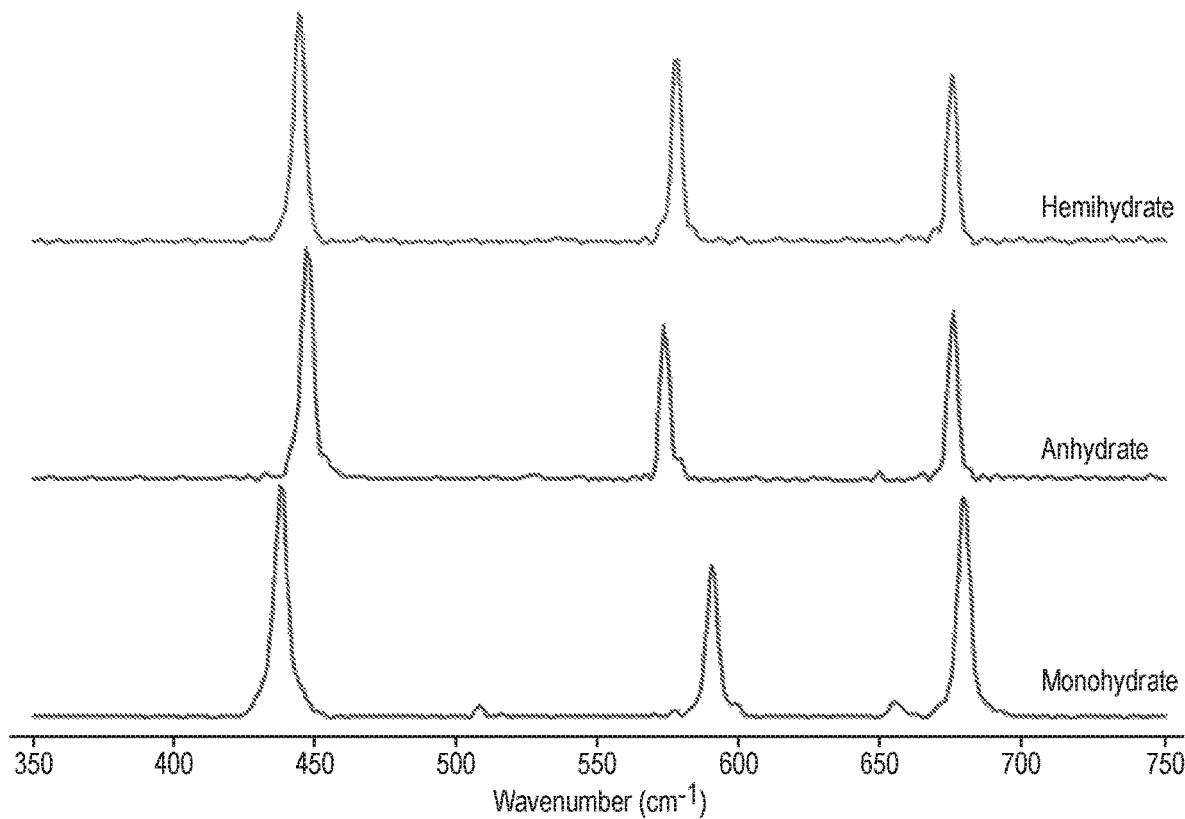
FIG. 4 shows Raman spectroscopy analysis of each of mercaptopurine monohydrate, anhydrate, and hemihydrate.

From these data, it was hypothesized that the hemihydrate would show increased bioavailability over the monohydrate form and pharmacokinetic studies in rats were conducted. The bioavailability of the three forms was determined by comparison of suspension and intravenous administration in order to quantify the effect. As shown in Table 1, the hemihydrate did in fact show increased pharmacokinetic parameters over the monohydrate form and also exceeded the performance of the anhydrate form. The hemihydrate is 2.7 times more bioavailable than the monohydrate form, which is higher than predicted based on the solubility. The hemihydrate form is also twice as bioavailable as the anhydrate, possibly due to increased resistance toward conversion of the hemihydrate compared to the anhydrate in aqueous solutions. Since the $T_{max}$ of the hemihydrate was much higher than the other two forms, it seems more compound was able to be absorbed overall even though over a somewhat longer time period, whereas the monohydrate and anhydrate were limited due to the solubility of the monohydrate form (FIG. 3).

TABLE 1

| | Monohydrate | Anhydrate | Hemihydrate |
|---|---|---|---|
| $T_{max}$ (hr) | 0.83 ± 0.29 | 0.83 ± 0.29 | 1.67 ± 0.58 |
| $C_{max}$ (µg/mL) | 0.23 ± 0.05 | 0.26 ± 0.01 | 0.28 ± 0.11 |
| AUC (µg · hr/mL) | 0.21 ± 0.06 | 0.43 ± 0.03 | 0.57 ± 0.12 |
| % F | 1.4 | 2.9 | 3.8 |
| $F_{rel}$ | 1 | 2 | 2.7 |

Overall, it can be seen that the newly discovered hemihydrate form of mercaptopurine shows many improved features in comparison to the known monohydrate and anhydrate forms. Not only does the hemihydrate have a higher thermal stability for dehydration than the monohydrate form, it is, to our knowledge, the highest dehydration temperature for any reported non-salt organic molecule. Also, the hemihydrate form showed better stability to aqueous conversion than the anhydrate form. Finally, the hemihydrate has double the water solubility as well as almost three times the in vivo bioavailability of the commercially used form. The mercaptopurine hemihydrate crystal form shows remarkable properties and could have an impact on the commercial market for mercaptopurine as a pharmaceutical.

Methods of Use

Provided herein are methods of using mercaptopurine hemihydrate. Mercaptopurine can be used as an anticancer therapeutic or in the treatment of autoimmune disorders. Mercaptopurine is used to treat acute lymphocytic leukemia (ALL), chronic myeloid leukemia (CML), Crohn's disease, and ulcerative colitis.

Mercaptopurine can be further administered with a second therapeutic agent, e.g., a second anti-cancer agent. Methotrexate and mercaptopurine have been approved as a combination therapy for cancer, e.g., ALL.

Pharmaceutical Formulations

Provided herein are pharmaceutical compositions comprising mercaptopurine hemihydrate and one or more pharmaceutically acceptable carriers. The pharmaceutical compositions are administered to a subject in need thereof by any route which makes the compound bioavailable. In one embodiment, the composition is a solid formulation adapted for oral administration. In another embodiment, the composition is a tablet, powder, or capsule; or the composition is a tablet. In one embodiment, the composition is a liquid formulation adapted for oral administration. In one embodiment, the composition is a liquid formulation adapted for parenteral administration. In another embodiment, the composition is a solution, suspension, or emulsion; or the composition is a solution. In another embodiment, solid form compositions can be converted, shortly before use, to liquid form compositions for either oral or parenteral administration. These particular solid form compositions are provided in unit dose form and as such are used to provide a single liquid dosage unit. These and other pharmaceutical compositions and processes for preparing the same are well known in the art. (See, for example, Remington: The Science and Practice of Pharmacy (D. B. Troy, Editor, 21st Edition, Lippincott, Williams & Wilkins, 2006).

EXAMPLES

Materials

Mercaptopurine monohydrate was obtained from Acros. Methanol was obtained from Fisher Scientific. Anhydrous methanol, 99.8%, AcroSeal, was obtained from Acros. All reagents were used without further purification.

Crystallization

Crystals of the monohydrate form were grown from methanol solutions (4 mg/mL) heated to 80° C. to dissolve all solids. Solutions were passed through a syringe filter into a 4 mL vial containing 2 mL $H_2O$. Vials were sealed and yellow block-shaped crystals grew after two days at room temperature.

Crystals of the hemihydrate form were grown from methanol solutions (4 mg/mL) heated to 80° C. to dissolve all solids. Solutions were passed through a syringe filter into a 4 mL vial containing 0.5 mL $H_2O$. Vials were sealed and yellow needle crystals grew after two days at room temperature.

Crystals of the anhydrate form were grown from anhydrous methanol solutions (4 mg/mL) in closed vials purged with $N_2$ heated to 80° C. to dissolve all solids. Solutions were passed through a syringe filter into new 30 mL vials. Solutions were concentrated under high vacuum to promote crystallization. Yellow needle crystals grew after several days at room temperature.

Computation of Vibrational Modes

Computation of the vibrational modes of isolated 6-mercaptopurine were performed in Spartan '14 V 1.1.2. The energy of the initial structure was minimized using molecular mechanics (MMFF). The equilibrium geometry was calculated using density functional theory B3LYP with the basis set 6-31G* in the gas phase and the predicted Raman spectra was calculated using the same methods.

Raman Spectroscopy

Raman spectra were collected using a Renishaw in Via Raman Microscope equipped with a Leica microscope, 633 nm laser, 1800 lines/mm grating, 50 µm slit, and a RenCam CCD detector. Spectra were collected in extended scan mode with a range of 300-1700 $cm^{-1}$ and then analyzed using the WiRE 3.4 software package (Renishaw). Calibration was performed using a silicon standard.

Raman spectra during slurry conversion were collected using a Kaiser Optical Systems Raman Rxn Microprobe equipped with a Multi-Rxn non-contact optic, 785 nm laser, and a multi-channel CCD detector. Spectra were collected with a range of 150-3425 $cm^{-1}$ and then analyzed using the HoloGRAMS 4.1 software package (Kaiser). Calibration was performed using a HoloLab Calibration Accessory and a cyclohexane standard.

Powder X-Ray Diffraction (PXRD)

Powder X-Ray diffraction patterns were collected on a Bruker D8 Advance diffractometer using Cu-Kα radiation (λ=1.54187 Å) and operating at 40 kV and 40 mA. Samples were prepared by grinding the crystals and pressing onto a glass slide. The pattern was collected by scanning 2θ from 5° to 60° with a step size of 0.02° and a step speed of 0.2 seconds. Powder patterns were processed using Jade 8 XRD Pattern Processing, Identification & Quantification analysis software (Materials Data, Inc). All powder patterns were compared to their respective simulated powder patterns from single crystal X-ray diffraction structures and were found to be in substantial agreement with the predicted patterns.

Variable temperature PXRD data were collected on a Rigaku SmartLab diffractometer using Cu-Kα radiation (λ=1.54187 Å) and operating at 40 kV and 44 mA. Samples were placed on a glass cover slip on top of a copper block that was heated at 2° C./min using a J-KEM Model 210 temperature controller. The setup was covered with a housing of Kapton to keep heat in but allow X-rays to penetrate. The spectrum was collected by scanning 2θ from 20 to 29° with a step size of 0.01° and a step speed of 0.1 seconds. Powder patterns were processed using Jade 8 XRD Pattern Processing, Identification & Quantification analysis software.[1]

Single Crystal Structure Determination

Single crystal X-ray diffraction data for the hemihydrate form was collected using a Rigaku AFC10K Saturn 944+ CCD-based X-ray diffractometer equipped with a low temperature device and Micromax-007HF Cu-target microfocus rotating anode (λ=1.54187 Å) operated at 1.2 kW power (40 kV, 30 mA). The X-ray intensities were measured at 85(1) K with the detector placed at a distance 42.00 mm from the crystal. The data was processed with CrystalClear 2.0 (Rigaku)[2] and corrected for absorption. The structure was solved and refined with the Bruker SHELXTL (version 2008/4)[3] software package, using the space group P2(1)/n with Z=4 for the formula 2($C_2H_4N_4S$), ($H_2O$). All non-hydrogen atoms were refined anisotropically with the hydrogen atoms placed in a combination of idealized and refined positions.

TABLE 2

|  | Monohydrate | Anhydrate | Hemihydrate |
|---|---|---|---|
| Chemical formula | $C_5H_6N_4S_1O_1$ | $C_5H_4N_4S_1$ | $C_{10}H_{10}N_8S_2O_1$ |
| Formula Weight (g/mol) | 170.19 | 152.18 | 161.19 |
| Crystal system | monoclinic | monoclinic | monoclinic |
| Space group | C2/c | $P2_1/n$ | $P2_1/n$ |
| a (Å) = | 15.294 (2) | 4.710 (1) | 9.361 (13) |
| b (Å) = | 7.731 (1) | 11.123 (1) | 11.069 (2) |
| c (Å) = | 12.379 (1) | 12.230 (1) | 13.091 (9) |
| α (°) = | 90 | 90 | 90 |
| β (°) = | 101 | 91.02 | 110.30 |
| γ (°) = | 90 | 90 | 90 |
| V (Å³) = | 716.876 | 640.630 | 1272.71 |
| Z' = | 1.0 | 1.0 | 1.0 |
| Z = | 8.0 | 4.0 | 4.0 |
| Temperature (K) = | 283-303 | 183 | 85 |

Differential Scanning Calorimetry (DSC)

Thermograms of the monohydrate and hemihydrate forms were recorded on a TA Instruments Q20 DSC. All experiments were run in Tzero™ hermetic aluminum DSC pans and studied under a nitrogen purge with a heating rate of 10° C./min, while covering the temperature range of 35° C. to 350° C. Calibration of the instrument was performed using an indium standard. Thermograms were analyzed using TA Universal Analysis 2000, V 4.5A.

Solubility

Solubility measurements were taken using a CrystalBreeder system (Technobis). Known amounts of solid compound and water were added to 0.3 mL clear round bottom vials equipped with a stir bar. The vials were sealed with a Teflon coated rubber crimped caps to prevent evaporation of solvent. Vials were loaded into one of the independently heated aluminum reactor blocks and turbidity measurements were taken using an LED light source and detector to measure particles in solution. Samples were heated to 85° C. at a rate of 0.2° C./min, held at 85° C. for 30 minutes, and then cooled to 0° C. at a rate of 0.2° C./min. Clear points were calculated based on the temperature at which 100% transmittance of solution was reached. Van't Hoff plots of concentration vs. time were produced from the data using CrystalClear software (Technobis) to determine the solubility of each form at different temperatures.

Pharmacokinetic Studies in Rats

Pharmacokinetic studies in rats were performed at Avastus Preclinical Services, Cambridge, Mass. All procedures were performed in accordance with the Guide for Care and Use of Laboratory Animals and were approved by the Avastus Institutional Animal Care and Use Committee. Male Sprague-Dawley rats weighing 200-300 g were dosed with mercaptopurine via oral gavage with a dosing volume of 5 mL/kg and a dose of 30 mg mercaptopurine form/kg or via IV administration at a dosing volume of 5 mL/kg and a dose of 15 mg mercaptopurine monohydrate/kg. Each group consisted of three rats, with one oral administration group for each form of mercaptopurine, and one IV administration group using the monohydrate form for reference. Blood samples were collected at time points of 15, 30, 60, 120, 240 minutes as well as 8 and 24 hours post dose. An additional time point at 5 minutes was taken for the IV administration group. Samples were centrifuged and the decanted plasma samples were stored at −80° C. until analysis.

PK Data Analysis

The plasma samples were analyzed via LC-MS/MS using an Agilent 6410 mass spectrometer coupled with an Agilent 1200 HPLC and a CTC PAL chilled autosampler, all controlled by MassHunter software (Agilent). All plasma samples were crashed with three volumes of methanol containing an analytical standard and centrifuged to remove precipitated protein before analysis. Samples were compared to a calibration curve prepared in rat blank plasma. Separation was performed on a C18 reverse phase HPLC column (Kinetex PFP, 2.6 μm, 2.1×50 mm) using an acetonitrile-water gradient system and peaks were analyzed by MS using ESI ionization in MRM mode. Peak area ratio to internal standard is used to interpolate plasma concentration for each sample from the calibration curve of peak area internal standard ratio to concentration. Pharmacokinetic parameters were fit using a custom WinNonlin analysis with PO dosing analysis. Area under the curve (AUC) for mercaptopurine was also calculated using the custom WinNonlin analysis. $C_{max}$ (maximum plasma concentration) and $T_{max}$ (time to reach maximum plasma concentration) were determined by visual inspection of the experimental data. The bioavailability (% F) was calculated from the following equation:

$$F = \frac{\text{oral } AUC\left(\frac{\mu g}{mL} \cdot hr\right)}{iv\ AUC\left(\frac{\mu g}{mL} \cdot hr\right)} \times \frac{iv\ \text{Dose}\left(\frac{mg}{kg}\right)}{\text{oral Dose}\left(\frac{mg}{kg}\right)} \times 100$$

$F_{rel}$ was calculated with respect to the monohydrate form.

What is claimed is:

1. Mercaptopurine hemihydrate.

2. The mercaptopurine hemihydrate of claim 1 having a dehydration temperature of greater than 200° C.

3. The mercaptopurine hemihydrate of claim 2 having a dehydration temperature of 240° C.

4. The mercaptopurine hemihydrate of claim 1 having at least 7 2Θ values selected from the group consisting of 10.59±0.1, 14.14±0.1, 15.86±0.1, 16.25±0.1, 18.83±0.1, 20.80±0.1, 20.42±0.1, 21.35±0.1, 24.93±0.1, 25.75±0.1, 26.02±0.1, 27.97±0.1, and 28.54±0.1°, as measured using CuKα radiation.

5. The mercaptopurine hemihydrate of claim 4, having 2Θ values 10.59±0.1, 14.14±0.1, 15.86±0.1, 16.25±0.1, 18.83±0.1, 20.80±0.1, 20.42±0.1, 21.35±0.1, 24.93±0.1, 25.75±0.1, 26.02±0.1, 27.97±0.1, and 28.54±0.1°, as measured using CuKα radiation.

6. The mercaptopurine hemihydrate of claim 1 having a crystal structure as represented by the following parameters as measured at 85K: a (Å) 9.361, b (Å) 11.069, c (Å) 13.091, α(°) 90, β(°) 110.3, and γ(°) 90.

7. The mercaptopurine hemihydrate of claim 1 having a Raman spectrum with wavenumber shifts 444±2, 577±2, and 674±2 $cm^{-1}$, as measured using a 633 nm laser.

8. A method of making the mercaptopurine hemihydrate of claim 1, comprising dissolving mercaptopurine monohydrate in methanol to form a methanol solution, contacting the methanol solution with water to form a solution, and crystallizing the mercaptopurine hemihydrate from the solution.

9. The method of claim 8, wherein the ratio (parts per volume) of methanol to water in the solution is 100:1 to less than 2:1.

10. The method of claim 9, wherein the ratio is 50:1 to 5:1.

* * * * *